United States Patent
Bevetek Mocnik et al.

(10) Patent No.: US 11,759,497 B2
(45) Date of Patent: Sep. 19, 2023

(54) DAPTOMYCIN FORMULATIONS

(71) Applicant: XELLIA PHARMACEUTICALS APS, Kobenhavn S (DK)

(72) Inventors: Anita Bevetek Mocnik, Zagreb (HR); Stipica Tomic, Zagreb (HR); Barbara Fumic, Zagreb (HR)

(73) Assignee: XELLIA PHARMACEUTICALS APS, Copenhagen S (DK)

( * ) Notice: Subject to any disclaimer, the term of this patent is extended or adjusted under 35 U.S.C. 154(b) by 0 days.

(21) Appl. No.: 16/642,462

(22) PCT Filed: Aug. 28, 2018

(86) PCT No.: PCT/EP2018/073141
§ 371 (c)(1),
(2) Date: Feb. 27, 2020

(87) PCT Pub. No.: WO2019/043008
PCT Pub. Date: Mar. 7, 2019

(65) Prior Publication Data
US 2020/0254054 A1 Aug. 13, 2020

Related U.S. Application Data

(60) Provisional application No. 62/663,247, filed on Apr. 26, 2018, provisional application No. 62/552,630, filed on Aug. 31, 2017.

(51) Int. Cl.
*A61K 38/12* (2006.01)
*A61P 31/04* (2006.01)
*A61K 9/19* (2006.01)
*A61K 31/198* (2006.01)
*A61K 31/4172* (2006.01)
*A61K 47/02* (2006.01)
*A61K 47/12* (2006.01)
*A61K 47/18* (2017.01)
*A61K 9/00* (2006.01)
*A61K 9/08* (2006.01)

(52) U.S. Cl.
CPC ........... *A61K 38/12* (2013.01); *A61K 9/19* (2013.01); *A61K 31/198* (2013.01); *A61K 31/4172* (2013.01); *A61K 47/02* (2013.01); *A61K 47/12* (2013.01); *A61K 47/183* (2013.01); *A61P 31/04* (2018.01); *A61K 9/0019* (2013.01); *A61K 9/08* (2013.01)

(58) Field of Classification Search
CPC ........ A61K 38/12; A61K 9/19; A61K 31/198; A61K 31/4172; A61K 47/02; A61K 47/12; A61K 47/183; A61K 9/0019; A61K 9/08; A61P 31/04
See application file for complete search history.

(56) References Cited

U.S. PATENT DOCUMENTS

| 4,885,243 | A | 12/1989 | Huber et al. | |
| 8,835,382 | B2* | 9/2014 | O'Connor | A61K 9/19 514/3.1 |
| 2007/0219124 | A1* | 9/2007 | Labischinski | A61K 9/0019 514/2.4 |
| 2011/0124551 | A1* | 5/2011 | Palepu | A61P 17/00 514/2.9 |
| 2015/0313958 | A1* | 11/2015 | Alexiou | A61K 9/0019 514/2.9 |
| 2023/0068866 | A1 | 3/2023 | Fumic | |

FOREIGN PATENT DOCUMENTS

| CN | 106943587 A | 7/2017 |
| JP | 2003535911 A | 12/2003 |
| JP | 2013511522 A | 4/2013 |
| JP | 2013511557 A | 4/2013 |
| WO | 2001097851 A2 | 12/2001 |
| WO | 2011062676 A1 | 5/2011 |
| WO | 2011063419 A2 | 5/2011 |
| WO | 2013103801 A1 | 7/2013 |
| WO | 2014041425 A1 | 3/2014 |
| WO | 2014045296 A2 | 3/2014 |
| WO | 2016098009 A1 | 6/2016 |
| WO | 2019043008 A1 | 3/2019 |

OTHER PUBLICATIONS

Tian_2006 [International Journal of Pharmaceutics, 2006, 310, 175-186] (Year: 2006).*
Tian_2007 [International Journal of Pharmaceutics, 2007, 335, 20-31] (Year: 2007).*
Ajmera et al (International Journal of Pharmaceutics, 2014, 463, 98-107) (Year: 2014).*
Mattern et al (Pharmaceutical Development and Technology, 1999, 4(2), 199-208) (Year: 1999).*
International Search Report and Written Opinion; International Application No. PCT/EP2018/073141; International Filing Date Aug. 28, 2018; dated Dec. 19, 2018; 14 pages.
Kirsch et al.; "Kinetics of the Aspartyl Transpeptidation of Daptomycin, a Novel Lipopeptide Antibiotic"; Pharmaceutical Research; 6(5); pp. 387-393; (1989).
Muangsiri et al., "The Kinetics of the Alkaline Degradation of Daptomycin"; Journal of Pharmaceutical Sciences; 90 (8), pp. 1066-1075; (2001).
Muangsiri et al.; "Studies on the Reactions Between Daptomycin and Glyceraldehyde"; International Journal of Pharmaceutics; 289; pp. 133-150; (2005).
Bulk Pharmaceutical Excipients—Certificate of Analysis, Chapter 1080, Docld: 1_GUID-A25D8181-39A6-472F-8F3F-F1A823853321_3_en-US, 2021.

(Continued)

*Primary Examiner* — Sudhakar Katakam
(74) *Attorney, Agent, or Firm* — CANTOR COLBURN LLP

(57) ABSTRACT

The present invention relates to compositions comprising daptomycin and at least one amino acid, methods of providing such compositions and the uses thereof.

14 Claims, No Drawings

(56) References Cited

OTHER PUBLICATIONS

Huber et al., The formation of daptomycin by supplying decanoic acid to Streptomyces roseosporus cultures producing the antibiotic complex A21978C, Journal of Biotechnology, 7:283-292, 1988.
English translation of Office Action for JP2020-505206 dated Jun. 29, 2022 (6 pages).
Frankenfeld, C. et al.; "Daptomycin: a comparison of two intravenous formulations"; Drug Design, Development and Therapy, vol. 12; 2018; pp. 1953-1958.
International Search Report and Written Opinion for International Application PCT/EP2021/054841; International Filing Date: Feb. 26, 2021; dated Jun. 4, 2021; 9 pages.
Goskonda, V. et al.; "Chemical Delivery Systems: Evaluation of Physicochemical Properties and Enzymatic Stability of Phenylephrone Derivatives"; Pharmaceutical Development and Technology, vol. 4, Issue No. 2; 1999; pp. 189-198; DOI: https://doi.org/10.1081/PDT-100101353.

\* cited by examiner

DAPTOMYCIN FORMULATIONS

CROSS REFERENCE TO RELATED APPLICATIONS

This application is a National Stage application of PCT/EP2018/073141, filed on Aug. 28, 2018, which claims the benefit of U.S. Provisional Application Numbers: 62/552,630 filed on Aug. 31, 2017, and 62/663,247, filed on Apr. 26, 2018, all of which are incorporated by reference in their entirety herein.

FIELD OF THE INVENTION

The present invention relates to compositions comprising daptomycin and at least one amino acid, methods of providing such compositions and the uses thereof.

BACKGROUND OF THE INVENTION

Lipopeptides represent a class of powerful anti-infective drugs which exhibit highly effective antibacterial action against multi-resistant bacteria, as well as antifungal activity. A wide variety of lipopeptide drugs, such as daptomycin, are now available on the market in order to fight invasive and often life-threatening infections.

Daptomycin is the first cyclic lipopeptide antibiotic approved by the U.S. Food and Drug Administration (FDA) in 2003, for the treatment of infections caused by Gram-positive pathogens, including methicillin- and vancomycin-resistant strains. Due to unique mechanism of action distinct from all other antimicrobial agents available in the market, daptomycin is able to overcome the mechanisms of resistance that many resistant strains have developed, and considering that rare incidences of clinical resistance to daptomycin are reported, the drug has become very important for current clinical practice.

Daptomycin (Formula 1) is composed of a decanoyl side chain attached to the N-terminus of a 13-amino acid peptide, wherein ten of the amino acids form a cyclic structure and the other three form a chain.

The cyclic section of the molecule is linked to the side chain through an ester bond between the C-terminal carboxyl group of kynurenine and the fourth residue (threonine).

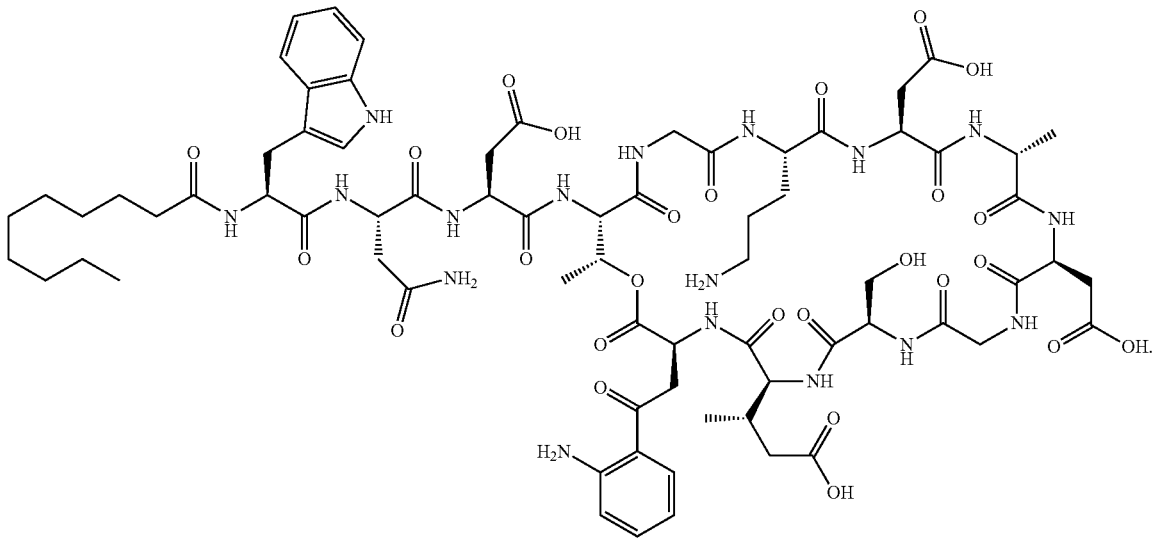

Formula 1

Molecular structure of daptomycin

According to the available literature, daptomycin is susceptible to hydrolytic degradation and is known to degrade by aspartyl transpeptidation at asp-9 residue in mildly acidic solutions.

According to Kirsch et al. *Pharmaceutical Research*, 1989, Muangsiri et al., *International Journal of Pharmaceutics*, 2005, and Muangsiri et al., *Journal of Pharmaceutical Sciences*, 2001, this degradation pathway involves the formation of a succinimido intermediate (anhydrodaptomycin) formed by attack of carbonyl carbon of Asp9 side chain and subsequent reversible formation of two aspartic acid isomers formed by rehydration of the anhydrodaptomycin succinimide.

Kirsch et al. *Pharmaceutical Research*, 1989, and Muangsiri et al., *Journal of Pharmaceutical Sciences*, 2001, page 1067, additionally disclose that unknown, parallel pathways of daptomycin loss have been observed and are thought to include asparaginyl deamidation, ester hydrolysis, and/or peptide bond cleavage.

The degradation pathways of daptomycin under acidic, neutral, and alkaline conditions are known as ester hydrolysis occurring in alkaline condition, aspartyl transpeptidation as the predominant pathway in the pH range of 3-6 and unknown degradation pathway which occurs at low pH. Besides pH dependent impurity formation, temperature is additional factor that causes degradation of daptomycin.

Daptomycin is currently commercially available in a form of lyophilized powder for intravenous infusion (Cubicin® and Cubicin RF®).

According to the Cubicin® label, the only inactive ingredient is sodium hydroxide, which is used for pH adjustment.

However, Cubicin®, according to the label, should be kept at refrigerated temperatures from to 2° C. to 8° C., and avoid exposing it to excessive heat.

Cubicin RF®, on the other hand, according to the available label, is supplied as lyophilized powder containing 500 mg of daptomycin and contains 713 mg of sucrose and sodium hydroxide used to adjust the pH. The pH of the solution upon reconstitution is 6.8. Cubicin RF® should be kept at 20° C. to 25° C. with excursions of temperature permitted to 15° C. to 30° C.

Application WO2011063419 discloses powder daptomycin compositions comprising daptomycin, sugar such as sucrose or glycine.

WO2014041425 discloses lyophilized daptomycin formulations comprising an additive, which can be a pharmaceutically acceptable antioxidant, a pharmaceutically acceptable organic acid or a pharmaceutically acceptable salt thereof, a pharmaceutically acceptable glucose derivative or a pharmaceutically acceptable salt thereof, or a combination thereof.

WO2014045296 relates to formulations comprising daptomycin and tocopheryl phosphate hydrolysate.

WO2013103801 reports powdered formulations comprising daptomycin and polyethylene glycol.

WO2016098009 relates to lyophilized compositions comprising daptomycin and a preservative.

SUMMARY OF THE INVENTION

Provided herein are stable pharmaceutical formulations comprising daptomycin and at least one amino acid or its pharmaceutically acceptable salt or derivative thereof.

In accordance with the present invention, provided stable pharmaceutical formulations comprise daptomycin and at least one amino acid selected from alanine, arginine, asparagine, histidine, isoleucine, lysine, ornithine, phenylalanine, proline, threonine, tryptophan and tyrosine or its pharmaceutically acceptable salt or derivative thereof.

In one aspect of the invention, daptomycin compositions comprise two or more amino acids or their pharmaceutically acceptable salts or derivatives thereof.

In further aspect of the invention, daptomycin compositions as disclosed herein comprise two or more amino acids or their pharmaceutically acceptable salts or derivatives thereof. According to yet a further aspect, at least one amino acid of the two or more amino acids is selected from alanine, arginine, asparagine, histidine, isoleucine, lysine, ornithine, phenylalanine, proline, threonine, tryptophan and tyrosine or its pharmaceutically acceptable salts or derivatives thereof.

In one aspect of the present invention, daptomycin composition comprise at least N-acetyl-D-alanine.

In one aspect of the present invention, daptomycin compositions comprise at least histidine or its pharmaceutically acceptable salt or derivative thereof.

In a further aspect of the present invention, the pharmaceutically acceptable salt is histidine hydrochloride.

According to yet an aspect, the daptomycin compositions of the invention comprise a second amino acid selected from alanine, arginine, asparagine, isoleucine, lysine, ornithine, phenylalanine, proline, threonine, tryptophan and tyrosine or its pharmaceutically acceptable salt or derivative thereof. In a further aspect, the daptomycin compositions of the invention comprise a second amino acid selected from arginine or ornithine. According to yet an aspect, said second amino acid is arginine.

Pharmaceutical compositions according to this invention have a molar ratio of daptomycin to at least one amino acid or its pharmaceutically acceptable salt or derivative thereof from about 1:0.5 to about 1:6 or from about 1:2 to about 1:5 or from about 1:3 to about 1:5.

In one aspect of the invention, daptomycin compositions comprise three or more amino acids selected from histidine, arginine and lysine; or histidine, proline and alanine; or proline, alanine and asparagine; or histidine, phenylalanine and tryptophan or their pharmaceutically acceptable salts. In a further aspect of the present invention, three or more amino acids or their pharmaceutically acceptable salts are selected from histidine hydrochloride, phenylalanine and tryptophan.

In a further aspect, the concentration of daptomycin in the compositions of the present invention is from about 0.5 mg/mL to about 500 mg/mL.

According to yet an aspect, the concentration of daptomycin in the compositions of the present invention is from about 20 mg/mL to about 400 mg/mL.

According to yet an aspect, the concentration of daptomycin in the compositions of the present invention is from about 50 mg/mL to about 300 mg/mL.

In further aspect, compositions of the present invention further comprise organic acid. According to a further aspect, the organic acid is selected from the group consisting of aconitic acid, tricarbalic acid, methanesulfonic acid, fumaric acid, glyceric acid, glycolic acid, gluconic acid, maleic acid, acetic acid, picolinic acid, formic acid, acetic acid, malic acid, citric acid, tartaric acid, succinic acid and lactic acid. According to a further aspect, compositions of the present invention comprise an organic acid selected from the group consisting of formic, acetic, malic, citric, tartaric, succinic and lactic acid.

Pharmaceutical compositions according to this invention have a molar ratio of daptomycin to an organic acid from about 0.5:1 to about 1:6, such as about 0.5:1, about 0.5:2, about 0.5:3, about 0.5:4, about 0.5:5, about 0.5:6, about 1:1, about 1:2, about 1:3, about 1:4, about 1:5 or about 1:6.

Encompassed by the present invention are formulations as disclosed above, further comprising calcium. According to one aspect, calcium in such compositions is selected from the group consisting of calcium chloride ($CaCl_2$), calcium chloride dyhidrate, calcium chloride hexahydrate, calcium citrate, Ca-α-D-heptagluconate or calcium acetate. According to yet another aspect, the daptomycin composition according to the present invention comprises calcium chloride dihydrate or calcium chloride hexahydrate.

Pharmaceutical compositions according to this invention have a molar ratio of daptomycin to calcium from about 1:1 to about 1:3, such as about 1:1, about 1:2 or about 1:3.

It was further discovered that addition of polyethylene glycols (PEG), for example PEG 400 or PEG 600, polypropylene glycol (PPG), polysorbates (PS) such as PS 20 or PS 80, alcohols such as ethanol or isobutyl alcohol, or mixtures thereof, to up to 3% V/V of the formulation significantly lowers reconstitution time of solid formulations.

In one aspect, daptomycin compositions according to the present inventions further comprise calcium and polyethylene glycols (PEG), for example PEG 400 or PEG 600, polypropylene glycol (PPG), polysorbates (PS) such as PS 20 or PS 80.

In one aspect, daptomycin compositions according to the present inventions further comprise calcium chloride dihydrate or calcium chloride hexahydrate and polypropylene glycol (PPG).

In one aspect, daptomycin compositions according to the present inventions, further comprise calcium chloride dihydrate or calcium chloride hexahydrate and polypropylene glycol (PPG).

In yet another aspect, a daptomycin composition is provided comprising at least one amino acid, calcium chloride dihydrate or calcium chloride hexahydrate and polypropylene glycol (PPG).

In yet another aspect, a daptomycin composition is provided comprising two amino acids, calcium chloride dihydrate or calcium chloride hexahydrate and polypropylene glycol (PPG).

In yet another aspect, a daptomycin composition is provided comprising L-His or a pharmaceutical acceptable salt thereof, L-arginine, calcium chloride and polypropylene glycol.

It was further found that addition of cyclodextrins such as hydroxypropyl-β-cyclodextrin or sulfobutylether-β-cyclodextrin, up to molar ratio of daptomycin to cyclodextrin from about 1:0.1 to about 1:1, such as about 1:0.1 to about 1:0.5, also improves reconstitution time of solid formulations.

In one aspect, a daptomycin composition is provided comprising calcium and cyclodextrins such as hydroxypropyl-β-cyclodextrin or sulfobutylether-β-cyclodextrin. In a further aspect of the invention, the daptomycin composition comprises two amino acids, calcium chloride and hydroxypropyl-β-cyclodextrin or sulfobutylether-β-cyclodextrin. Additionally, compositions of the present invention may further comprise one or more pharmaceutically acceptable excipients such as antioxidants, surfactants, lipids, sugars, amino sugars, complexing agents, preservatives, stabilizers, bulking agents, buffers, diluents, vehicles, solubilizers and binders.

In one aspect of the present invention, amino sugar is meglumine.

Pharmaceutical compositions according to this invention have a molar ratio of daptomycin to an amino sugar, such as meglumine, from about 1:1 to about 1:3, such as about 1:1, about 1:2 or about 1:3.

Encompassed by the present invention are compositions as disclosed above, wherein the composition is solid. According to one aspect the daptomycin composition according to the invention, the composition is lyophilized, spray-dried or fluid bed dried.

Formulations provided herein can be stored at room temperature (25° C.), below room temperature, such as temperature of about 20° C., about 15° C., about 10° C., and refrigerated conditions such as 2-8° C.

The pharmaceutical compositions according to the invention comprise about 200 mg/ml to about 400 mg/ml daptomycin; wherein the pharmaceutical composition comprises two amino acids or its pharmaceutically acceptable salt or derivative thereof selected from alanine, arginine, asparagine, histidine, histidine hydrochloride, isoleucine, lysine, N-acetyl-D-alanine, ornithine, phenylalanine, proline, threonine, tryptophan and tyrosine; wherein the molar ratio of daptomycin to each amino acid is about 1:0.5 to about 1:6; wherein the pharmaceutical composition comprises calcium; wherein the molar ratio of daptomycin to calcium is about 1:1 to about 1:3.

According to one aspect, the pharmaceutical compositions according to the invention comprise daptomycin, calcium, histidine and arginine in a molar ratio of about 1:1:3:4.

According to yet an aspect, the pharmaceutical compositions according to the invention further comprise polypropylene glycol in an amount of about 0.1 to about 3% v/v.

In a further aspect of the present invention relates to pharmaceutical compositions comprising polypropylene glycol in an amount of about 0.5% v/v.

In yet a further aspect, the pharmaceutical composition according to the invention comprise polypropylene glycol in an amount of about 0.25% v/v.

In one aspect of the present invention, compositions are prepared by a process of providing a solution of daptomycin and at least one amino acid; adjusting the pH of such solution to pH from about 3 to about 9 with a suitable pH adjusting agent; and lyophilizing, spray drying or fluid bed drying such composition to a solid composition.

In one aspect of the present invention, compositions are prepared by a process of providing a solution of daptomycin and at least one amino acid; adjusting the pH of such solution to pH from about 4 to about 7 with a suitable pH adjusting agent; and lyophilizing, spray drying or fluid bed drying such composition to a solid composition.

In a further aspect, the process according to the invention further comprise the step of solid composition reconstitution with a suitable solvent/diluent.

In yet another aspect, the process of the present invention further comprising the step of dilution with a suitable solvent/diluent.

Furthermore, the present invention provides pharmaceutical composition for use in treatment of microbial infections, particularly caused by Gram-positive organisms.

Finally, the present invention provides in one aspect a pharmaceutical composition for use in treatment of skin and soft-tissue infections (cSSTI), *Staphylococcus aureus* bloodstream infections (bacteremia).

Other objects, features and advantages of the present invention will become apparent from the following detailed description and examples. It should be understood, however, that the detailed description and the examples, while indicating specific embodiments of the invention, are given by way of illustration only, and are not intended to limit the breadth or scope of the invention concepts in any manner.

DETAILED DESCRIPTION OF THE INVENTION

Stable and pharmaceutically acceptable compositions of daptomycin have been discovered and reported herein.

Surprisingly it was discovered when daptomycin is formulated according to the present invention, formations of degradation products is retarded, and accordingly, such formulations are stable both chemically and physically and provide more flexible storage conditions and handling.

Term "stable" as used herein, refers to a pharmaceutical formulation containing daptomycin having sufficient stability to have utility as a pharmaceutical product.

The disclosed formulations exhibit acceptable stability with regard to retaining the daptomycin efficacy and potency, avoid unacceptable degradation of active substance to undesired related substances, and retain pharmaceutically desirable appearance.

By terms "pharmaceutical composition" or "pharmaceutically acceptable composition" as used herein, is meant a composition that is suitable for veterinary use as well as human pharmaceutical use, wherein such composition is generally safe, relatively non-toxic and does not cause unacceptable side effects, and contains pharmaceutically acceptable excipients, e.g. without limitation to solvents, carriers, antioxidants, surfactants, lipids, sugars, amino sugars, organic acids, complexing agents, preservatives, stabilizers, bulking agents, buffers, diluents, vehicles, solubilizers and binders.

As used herein, the terms "pharmaceutical composition", "pharmaceutical formulation", "composition" and "formulation" are used interchangeably.

As used herein, by the term "amino acid" it is meant amino acid but also pharmaceutically acceptable salts and derivatives thereof.

In view of excipients, without limitation to solvents, carriers, antioxidants, surfactants, lipids, sugars, amino sugars, organic acids, complexing agents, preservatives, stabilizers, bulking agents, buffers, diluents, vehicles, solubilizers and binders etc., as used herein, "pharmaceutically acceptable" is meant that they are useful in preparing a pharmaceutical composition that is generally non-toxic and neither biologically nor otherwise undesirable, further that they do not cause unacceptable loss of pharmacological activity of the drug in question, and are acceptable for use in treatment of humans and/or animals.

The language "therapeutically effective amount" of the daptomycin compound, as used herein, refers to an amount of daptomycin administered to a patient sufficient to produce a therapeutic response to one or more of the symptoms of the disease being treated.

The "pH adjusting agent" is an agent that can change—increase or decrease, the pH of a solution e.g. an acid, a base or a salt thereof.

As used herein, the term "about" is defined as ±10% of the numerical value or range in question.

As used herein, the term "targeted pH" is defined as ±0.1 of the numerical value or range in question.

Amino acid derivatives, as disclosed in the present invention, are defined as any derivative of an amino acid resulting from reaction at an amino group, carboxy group, side-chain functional group, or from the replacement of any hydrogen by a heteroatom.

Amino sugars, as disclosed in the present invention, are defined as chemical compounds that have a sugar backbone, in which one of the hydroxyl groups is replaced by an amino group or substituted amino group. Derivatives of amine-containing sugars, such as N-acetylglucosamine, are also part of this group.

Formulations according to this invention show notably lower impurities level at initial time point, determined by HPLC analysis, as well as other time points, determined by HPLC, when stored under typical storage conditions, in comparison to composition of daptomycin without any amino acid when stored under same conditions.

Obtained results additionally show that increase of impurities over time is significantly retarded when compositions according to this invention are stored under typical storage conditions.

Stable pharmaceutical compositions of daptomycin, according to the present invention, have sufficient stability to allow typical storage at a convenient temperature, wherein the typical storage temperature range is from 2° C. to 30° C., for a reasonable period of time.

It has been shown that pharmaceutically acceptable formulations of daptomycin, according to the present invention are stable over the course of typical storage conditions, including time periods of about 7 days (1 week), about 14 days (2 weeks), about 30 days (1 month), about 60 days (2 months), about 150 days (5 months), about 180 days (6 months), about 12 months (1 year) and longer at temperatures of about 25° C. (room temperature), below room temperatures, and refrigerated temperatures, for example, about 2-8° C.

Preferably, the formulations of the present invention are stored at room temperature, e.g. 25° C.

In one embodiment of the present invention, stable and pharmaceutically acceptable compositions of daptomycin comprise at least one amino acid or its pharmaceutically acceptable salt or derivative thereof.

In accordance of the present invention, provided stable pharmaceutical formulations comprise daptomycin and at least one amino acid or its pharmaceutically acceptable salt or derivative thereof selected from alanine, arginine, asparagine, histidine, histidine hydrochloride, isoleucine, lysine, N-acetyl-D-alanine, ornithine, phenylalanine, proline, threonine, tryptophan and tyrosine.

In one aspect of the invention, daptomycin compositions as disclosed herein comprise two or more amino acids or their pharmaceutically acceptable salts or derivatives thereof.

Formulations of the present invention comprise therapeutically effective amounts of daptomycin, wherein therapeutically effective amounts include concentrations ranging from about 0.5 mg/mL to about 500 mg/mL, from about 20 mg/mL to about 400 mg/mL, from about 50 mg/mL to about 300 mg/mL, such as concentration of about 0.5 mg/mL, about 1 mg/mL, about 3 mg/mL, about 5 mg/mL, about 10 mg/mL, about 15 mg/mL, about 20 mg/mL, about 25 mg/mL, about 30 mg/mL, about 35 mg/mL, about 40 mg/mL, about 50 mg/mL, about 60 mg/mL, about 70 mg/mL, about 80 mg/mL, about 90 mg/mL, about 100 mg/mL, about 110 mg/mL, about 120 mg/mL, about 130 mg/mL, about 140 mg/mL, about 150 mg/mL, about 160 mg/mL, about 170 mg/mL, about 180 mg/mL, about 190 mg/mL, about 200 mg/mL, about 210 mg/mL, about 220 mg/mL, about 230 mg/mL, about 240 mg/mL, about 250 mg/mL, about 260 mg/mL, about 270 mg/mL, about 280 mg/mL, about 290 mg/mL, about 300 mg/mL, about 350 mg/mL, about 400 mg/mL, about 450 mg/mL and about 500 mg/mL.

According to the invention, formulations can be reconstituted with suitable diluent(s).

Additionally, in order to achieve lower therapeutically effective concentrations of daptomycin, compositions according to the invention may be further diluted with suitable diluent(s).

The "diluent(s)" of interest herein is one which is pharmaceutically acceptable; safe and non-toxic for administration to a human, and is suitable for the preparation of a reconstituted or further diluted formulation.

Exemplary diluents include Sterile water for injection, Bacteriostatic water for injection (BWFI), sterile saline solution (0.9% Sodium Chloride), Ringer's solution or dextrose solution.

The formulations of daptomycin described herein are intended to be administered via injection, for example subcutaneously, intracutaneously, intravenously, intramuscularly, intraarticularly, intrasynovially, intrasternally, intrathecally, intralesionally, intracranially or via infusion.

Also within the scope of the invention are uses of pharmaceutical formulations of daptomycin, as disclosed herein, for treating diseases caused by Gram positive bacteria such as complicated skin and soft-tissue infections (cSSTI), *Staphylococcus aureus* bloodstream infections (bacteremia), including those with right-sided infective endocarditis (RIE).

These uses comprise administering to the patient a therapeutically effective amount of formulations according to this invention or administering to the patient a therapeutically effective amount of preparation prepared from a pharmaceutical formulation of the present invention.

Methods

Compositions according to this invention were prepared by providing a liquid solution of daptomycin and one amino acid or by providing a liquid solution of daptomycin and two or more amino acids, adjusting the pH of such solutions with a suitable pH adjusting agent to a desired pH, transferring such solutions to vials to achieve desired amount of daptomycin per vial and lyophilization.

After lyophilization, initial time point level of impurities was determined by HPLC and afterwards vials were loaded to stability chambers at different storage conditions, such as 60° C., 25° C./60% RH and 40° C./75% RH.

In order to determine formation of impurities and stability of daptomycin in formulations according to the present invention, vials were taken from stability chambers at various time points such as 45 hours, 1 month, 2 months etc. and analyzed by HPLC.

Analysis of the formulations of the present invention can be performed using techniques known in the art such as HPLC technique, including HPLC such as disclosed in WO2011063419, or gas chromatography.

EXAMPLES

List of Abbreviations Used

AA—Amino acid
DAP—Daptomycin
RH—Relative humidity
WFI—Water for injection
D—Day(s)
M—Month(s)
W—Week(s)
Ala—Alanine
Arg—Arginine
Asn—Asparagine
His—Histidine
His HCl—Histidine Hydrochloride
Ile—Isoleucine
Lys—Lysine
NADA—N-acetyl-D-Alanine
Orn—Ornithine
Phe—Phenylalanine
Pro—Proline
Thr—Threonine
Trp—Tryptophan
EtOH—Ethanol
IBA—Isobutyl alcohol
PEG 400/600—Polyethylene glycol 400 or 600
PPG—Polypropylene glycol
PS 20/80—Polysorbate 20 or 80
HPPCD—Hydroxypropyl-β-cyclodextrin
SBEIβCD—Sulfobutylether-β-cyclodextrin
$TP_n$—Value of total impurities at time point different than initial, for example: 45 hrs, 1 month, 2 months etc. at different storage conditions such as 25° C./60% RH, 40° C./75% RH and 60° C., determined by HPLC
Δ—Calculated increase of total impurities:

Δ Total impurities (%)=Total impurities value at $TP_n$ (%)−Total impurities initial value (%)

Total impurities % —Calculated using Area percentage method: A determination of the level of analyte, As, compared with the total area of all the sample-related peaks in the chromatogram, Σ(As)i Area % of As=[As/Σ(As)$i$]×100

Example 1

Daptomycin (6.773 g, given the assay on anhydrous basis of daptomycin of 100.3% and water content of 3.1%), was added in solution of desired amino acid or two or more amino acids in WFI. Molar ratio varied from molar ratio of daptomycin to one amino, or to each individual amino acid if two or more were added, of about 1:0.5 to about 1:6, such as 1:0.5, 1:1, 1:2, 1:3, 1:4, 1:5 and 1:6.

The contents were then stirred, protected from atmosphere, using a magnetic stirrer. pH was adjusted using 5M NaOH solution. The solution was then transferred to a volumetric flask and WFI was added to make up to volume of 50 mL.

The solution was mixed to ensure homogeneity, filtered through a 0.2 μm filter, transferred to vials and lyophilized.

TABLE 1a

Stability of daptomycin compositions at targeted pH 5.8 when stabilized with one amino acid

| Formulation Molar ratio | Time point/ Condition $TP_n$ | Total impurities % | Δ Total impurities % |
|---|---|---|---|
| Without amino acid | INITIAL | 4.2 | — |
|  | 45 hrs/60° C. | 6.4 | 2.2 |
| DAP:L-Arg = 1:1 | INITIAL | 3.9 | — |
|  | 45 hrs/60° C. | 5.9 | 2.0 |
| DAP:L-His = 1:0.5 | INITIAL | 3.5 | — |
|  | 45 hrs/60° C. | 5.5 | 2.0 |
|  | 3M at 40° C./75% RH | 6.9 | 3.4 |
| DAP:L-His = 1:1 | INITIAL | 3.5 | — |
|  | 45 hrs/60° C. | 5.3 | 1.8 |
|  | 3M at 40° C./75% RH | 6.7 | 3.2 |
| DAP:L-His = 1:2 | INITIAL | 3.5 | — |
|  | 45 hrs/60° C. | 4.9 | 1.4 |
| DAP:L-His = 1:3 | INITIAL | 3.6 | — |
|  | 45 hrs/60° C. | 4.7 | 1.1 |
|  | 1M at 40° C./75% RH | 3.7 | 0.1 |
| DAP:L-Thr = 1:5 | INITIAL | 3.6 | — |
|  | 45 hrs/60° C. | 4.4 | 0.8 |
|  | 2M at 25° C./60% RH | 4.0 | 0.4 |
|  | 60% RH | 4.6 | 1.0 |
|  | 2M at 40° C./75% RH | | |
| DAP:L-His HCl = 1:5 | INITIAL | 3.8 | — |
|  | 45 hrs/60° C. | 4.1 | 0.3 |
|  | 1M at 40° C./75% RH | 4.3 | 0.5 |
| DAP:L-Lys = 1:6 | INITIAL | 4.0 | — |
|  | 45 hrs/60° C. | 5.2 | 1.2 |
| DAP:NADA = 1:6 | INITIAL | 3.8 | — |
|  | 45 hrs/60° C. | 4.7 | 0.9 |

TABLE 1b

Stability of daptomycin compositions at targeted pH 5.8 when stabilized with two amino acids

| Formulation Molar ratio | Time point/ Condition $TP_n$ | Total impurities % | Δ Total impurities % |
|---|---|---|---|
| Without amino acid | INITIAL | 4.2 | — |
|  | 45 hrs/60° C. | 6.4 | 2.2 |
| DAP:L-His:L-Arg = 1:1:1 | INITIAL | 3.8 | — |
|  | 45 hrs/60° C. | 5.3 | 1.5 |
| DAP:L-His:L-Arg = 1:3:3 | INITIAL | 3.7 | — |
|  | 45 hrs/60° C. | 4.1 | 0.4 |
|  | 1M at 25° C./ 60% RH | 3.7 | 0.0 |
|  | 1M at 40° C./ 75% RH | 3.9 | 0.2 |
| DAP:L-His:L-Orn HCl = 1:3:3 | INITIAL | 3.6 | — |
|  | 45 hrs/60° C. | 4.3 | 0.7 |
| DAP:L-Lys:NADA = 1:3:3 | INITIAL | 3.7 | — |
|  | 45 hrs/60° C. | 4.6 | 0.9 |
| DAP:L-Pro:L-Ala = 1:3:3 | INITIAL | 4.1 | — |
|  | 45 hrs/60° C. | 5.1 | 1.0 |
|  | 3M at 40° C./ 75% RH | 5.4 | 1.3 |

TABLE 1c

Stability of daptomycin compositions at targeted pH 5.8 when stabilized with three amino acids

| Formulation Molar ratio | Time point/ Condition $TP_n$ | Total impurities % | Δ Total impurities % |
|---|---|---|---|
| Without amino acid | INITIAL | 4.2 | — |
|  | 45 hrs/60° C. | 6.4 | 2.2 |
| DAP:L-His:L-Arg:L-Lys = 1:1:1:1 | INITIAL | 3.8 | — |
|  | 45 hrs/60° C. | 4.9 | 1.1 |
| DAP:L-His:L-Arg:L-Lys = 1:2:2:2 | INITIAL | 3.8 | — |
|  | 45 hrs/60° C. | 4.3 | 0.5 |
|  | 1M at 25° C./ 60% RH | 3.8 | 0.0 |
|  | 1M at 40° C./ 75% RH | 4.0 | 0.2 |
| DAP:L-His:L-Pro:L-Ala = 1:2:2:2 | INITIAL | 4.2 | — |
|  | 45 hrs/60° C. | 4.7 | 0.5 |
|  | 3M at 40° C./ 75% RH | 4.8 | 0.6 |
| DAP:L-Pro:L-Ala:L-Asn = 1:2:2:2 | INITIAL | 4.3 | — |
|  | 45 hrs/60° C. | 5.2 | 0.9 |
|  | 3M at 40° C./ 75% RH | 5.6 | 1.3 |
| DAP:L-His HCl:L-Phe:L-Trp = 1:5:1:1 | INITIAL | 4.0 | — |
|  | 45 hrs/60° C. | 4.3 | 0.3 |
|  | 2M at 40° C./ 75% RH | 4.4 | 0.4 |
| DAP:L-His:L-Phe:L-Trp = 1:3:1:1 | INITIAL | 3.8 | — |
|  | 45 hrs/60° C. | 4.0 | 0.2 |
|  | 2M at 40° C./ 75% RH | 4.3 | 0.5 |

TABLE 1d

Stability of daptomycin compositions at targeted pH 4.7

| Formulation Molar ratio | Time point/ Condition $TP_n$ | Total impurities % | Δ Total impurities % |
|---|---|---|---|
| Without amino acid | INITIAL | 3.2 | — |
|  | 45 hrs/60° C. | 5.1 | 1.9 |
| DAP:L-His = 1:1 | INITIAL | 3.6 | — |
|  | 45 hrs/60° C. | 5.0 | 1.4 |
| DAP:L-His:L-Arg:L-Lys = 1:1:1:1 | INITIAL | 3.7 | — |
|  | 45 hrs/60° C. | 4.3 | 0.6 |

TABLE 1e

Stability of daptomycin compositions at targeted pH 7

| Formulation Molar ratio | Time point/ Condition $TP_n$ | Total impurities % | Δ Total impurities % |
|---|---|---|---|
| Without amino acid | INITIAL | 4.2 | — |
|  | 45 hrs/60° C. | 7.6 | 3.4 |
| DAP:L-His = 1:1 | INITIAL | 3.6 | — |
|  | 45 hrs/60° C. | 6.1 | 2.5 |
| DAP:L-His = 1:3 | INITIAL | 4.2 | — |
|  | 45 hrs/60° C. | 5.1 | 0.9 |
| DAP:L-His HCl = 1:5 | INITIAL | 4.0 | — |
|  | 45 hrs/60° C. | 4.8 | 0.8 |
| DAP:L-Arg = 1:3 | INITIAL | 3.8 | — |
|  | 45 hrs/60° C. | 5.4 | 1.6 |

Example 2

In 35 ml of WFI, meglumine was added. Then desired amino acid (one or two or more amino acids) was dissolved. Daptomycin (6.773 g, given the assay on anhydrous basis of daptomycin of 100.3% and water content of 3.1%), was added to solution.

Molar ratio varied from molar ratio of daptomycin to one amino acid, or to each individual amino acid if two or more were added, of about 1:0.5 to about 1:6, such as 1:0.5, 1:1, 1:2, 1:3, 1:4, 1:4.5, 1:5 and 1:6.

Molar ratio varied from molar ratio of daptomycin to meglumine of about 1:1 to about 1:3, such as 1:1, 1:2 and 1:3.

The contents were then stirred using a magnetic stirrer and protected from atmosphere. pH was adjusted using 5M NaOH solution.

The solution was then transferred to a volumetric flask and WFI was added to make up to volume of 50 mL. The solution was mixed to ensure homogeneity, filtered through a 0.2 µm filter, transferred to vials and lyophilized.

TABLE 2a

Stability of daptomycin compositions further comprising meglumine at targeted pH 7.0

| Formulation Molar ratio | Time point/ Condition $TP_n$ | Total impurities % | Δ Total impurities % |
|---|---|---|---|
| Without amino acid | INITIAL | 4.2 | — |
|  | 45 hrs/60° C. | 7.6 | 3.4 |
| DAP:L-His:L-Arg:L-Lys = 1:1:1:1 | INITIAL | 3.8 | — |
|  | 45 hrs/60° C. | 5.5 | 1.7 |
| DAP:Meglumine = 1:1 | | | |

TABLE 2b

Stability of daptomycin compositions further comprising meglumine at targeted pH 5.8

| Formulation Molar ratio | Time point/ Condition $TP_n$ | Total impurities % | Δ Total impurities % |
|---|---|---|---|
| Without amino acid | INITIAL | 4.2 | — |
|  | 45 hrs/60° C. | 6.4 | 2.2 |
| DAP:L-His:L-Arg:L-Lys = 1:1:1:1 DAP:Meglumine = 1:1 | INITIAL | 3.9 | — |
|  | 45 hrs/60° C. | 4.5 | 0.6 |
| DAP:L-His:L-Arg:L-Lys = 1:1:1:1 DAP:Meglumine = 1:2 | INITIAL | 3.8 | — |
|  | 45 hrs/60° C. | 4.5 | 0.7 |
| DAP:L-Pro:L-Ala = 1:3:3 DAP:Meglumine = 1:1 | INITIAL | 3.6 | — |
|  | 45 hrs/60° C. | 4.6 | 1.0 |
| DAP:L-Pro:L-Ala = 1:4.5:3 DAP:Meglumine = 1:1 | INITIAL | 3.7 | — |
|  | 45 hrs/60° C. | 4.9 | 1.2 |
| DAP:L-Ile = 1:3 DAP:Meglumine = 1:1 | INITIAL | 3.9 | — |
|  | 45 hrs/60° C. | 5.9 | 2.0 |
| DAP:L-Thr = 1:5 DAP:Meglumine = 1:1 | INITIAL | 3.6 | — |
|  | 45 hrs/60° C. | 4.5 | 0.9 |
|  | 2M at 25° C./ 60% RH | 4.0 | 0.4 |
|  | 2M at 40° C./ 75% RH | 4.5 | 0.9 |
| DAP:L-His = 1:3 DAP:Meglumine = 1:1 | INITIAL | 3.7 | — |
|  | 45 hrs/60° C. | 4.3 | 0.6 |
| DAP:L-His HCl = 1:5 DAP:Meglumine = 1:1 | INITIAL | 3.9 | — |
|  | 45 hrs/60° C. | 4.1 | 0.2 |

Example 3

Amino acid (one or more) was added in 35 ml WFI. Then, desired organic acid was added. Daptomycin (6.773 g, given the assay on anhydrous basis of daptomycin of 100.3% and water content of 3.1%), was added to solution.

Molar ratio varied from molar ratio of daptomycin to one amino acid, or to each individual amino acid if two or more were added of about 1:0.5 to about 1:6, such as 1:0.5, 1:1, 1:2, 1:3, 1:4, 1:4.5, 1:5 and 1:6.

The contents were then stirred using a magnetic stirrer and protected from atmosphere. pH was adjusted using 5M NaOH solution. The solution was then transferred to a volumetric flask and WFI was added to make up to volume of 50 mL. The solution was mixed to ensure homogeneity, filtered through a 0.2 μm filter, transferred to vials and lyophilized.

TABLE 3

Stability of daptomycin compositions at targeted pH 5.8 when stabilized with one or more amino acids and organic acid

| Formulation Molar ratio | Time point/ Condition $TP_n$ | Total impurities % | Δ Total impurities % |
|---|---|---|---|
| DAP without amino acid or organic acid | INITIAL | 4.2 | — |
|  | 45 hrs/60° C. | 6.4 | 2.2 |
| DAP:His:Citric acid = 1:6:2 | INITIAL | 3.5 | — |
|  | 45 hrs/60° C. | 4.2 | 0.7 |
| DAP:His:Tartaric acid = 1:6:3 | INITIAL | 3.9 | — |
|  | 45 hrs/60° C. | 4.7 | 0.8 |
| DAP:His:Succinic acid = 1:6:3 | INITIAL | 3.7 | — |
|  | 45 hrs/60° C. | 5.2 | 1.5 |
| DAP:His:Lactic acid = 1:6:6 | INITIAL | 4.0 | — |
|  | 45 hrs/60° C. | 5.7 | 1.7 |
| DAP:L-His:L-Trp:L-Phe:Citric acid = 1:3:1:1:2 | INITIAL | 3.7 | — |
|  | 45 hrs/60° C. | 4.1 | 0.4 |
|  | 3M at 40° C./ 75% RH | 4.1 | 0.4 |
| DAP:L-Ala:Citric acid = 1:3:2 | INITIAL | 4.0 | — |
|  | 45 hrs/60° C. | 4.9 | 0.9 |
|  | 3M at 25° C./ 60% RH | 4.5 | 0.5 |
|  | 3M at 40° C./ 75% RH | 5.4 | 1.4 |

Example 4

Amino acids were added in 35 ml WFI. Then, selected source of calcium was added. Daptomycin (6.773 g, given the assay on anhydrous basis of daptomycin of 100.3% and water content of 3.1%), was added to solution.

The contents were then stirred using a magnetic stirrer and protected from atmosphere. pH was adjusted using 5M HCl solution. The solution was then transferred to a volumetric flask and WFI was added to make up to volume of 50 mL. The solution was mixed to ensure homogeneity, filtered through a 0.2 μm filter, transferred to vials and lyophilized.

TABLE 4a

Stability of daptomycin compositions at targeted pH 6.6 when stabilized with two amino acids and comprising source of calcium

| Formulation Molar ratio | Time point/ Condition $TP_n$ | Total impurities % | Δ Total impurities % |
|---|---|---|---|
| DAP:CaCl$_2$ × 6H$_2$O:L-His:L-Arg = 1:1:3:3 | INITIAL | 3.5 | — |
|  | 45 hrs/60° C. | 3.7 | 0.2 |

TABLE 4b

Stability of daptomycin compositions at targeted pH 7.2 when stabilized with two more amino acids and comprising source of calcium

| Formulation Molar ratio | Time point/ Condition $TP_n$ | Total impurities % | Δ Total impurities % |
|---|---|---|---|
| DAP:CaCl$_2$ × 6H$_2$O:L-His:HCl:L-Arg = 1:1:3:3 | INITIAL | 4.9 | — |
|  | 45 hrs/60° C. | 5.3 | 0.4 |
| DAP:CaCl$_2$ × 6H$_2$O:L-His:L-Arg = 1:1:3:3 | INITIAL | 3.8 | — |
|  | 45 hrs/60° C. | 4.3 | 0.5 |

Example 5

Formulations according to the present invention, although stable, have different reconstitution times to up to 15 minutes. Various additional excipients were added in order to reduce the reconstitution time. Results are shown in Tables 5a and 5b.

Amino acids were added in 35 ml WFI. Then, selected source of calcium and selected excipient for improvement of reconstitution time were added. Daptomycin (6.773 g, given the assay on anhydrous basis of daptomycin of 100.3% and water content of 3.1%), was added to solution.

The contents were then stirred using a magnetic stirrer and protected from atmosphere. pH was adjusted using 5M HCl solution to targeted pH. The solution was then transferred to a volumetric flask and WFI was added to make up to volume of 50 mL. The solution was mixed to ensure homogeneity, filtered through a 0.2 μm filter, transferred to vials and lyophilized.

Reconstitution time, as presented in Tables 5a and 5b was measured after lyophilization (initial) and after stability testing, wherein vials were reconstituted with 10.0 mL of WFI.

TABLE 5a

Stability and reconstitution times of daptomycin compositions at targeted pH 6.6

| Formulation Molar ratio | Time point/ Condition TP$_n$ | Total impurities % | Δ Total impurities % | Reconstitution time |
|---|---|---|---|---|
| DAP:CaCl$_2$ x 6H$_2$O:L-His:L-Arg = 1:1:3:3 | INITIAL<br>45 hrs/60° C. | 3.5<br>3.7 | —<br>0.2 | 6:00<br>6:20 |
| DAP:CaCl$_2$ x 6H$_2$O:L-His:L-Arg = 1:1:3:3 + 0.5% (V/V) PEG 400 | INITIAL<br>45 hrs/60° C. | 3.6<br>3.9 | —<br>0.3 | 4:00<br>4:00 |
| DAP:CaCl$_2$ x 6H$_2$O:L-His:L-Arg = 1:1:3:3 + 1% (V/V) PEG 400 | INITIAL<br>45 hrs/60° C. | 3.5<br>3.6 | —<br>0.1 | 2:10<br>2:30 |
| DAP:CaCl$_2$ x 6H$_2$O:L-His:L-Arg = 1:1:3:3 + 0.5% (V/V) PS 80 | INITIAL<br>45 hrs/60° C. | 3.4<br>3.8 | —<br>0.4 | 2:30<br>2:30 |
| DAP:CaCl$_2$ x 6H$_2$O:L-His:L-Arg = 1:1:3:3 + 0.5% (V/V) PS 20 | INITIAL<br>45 hrs/60° C. | 3.5<br>3.7 | —<br>0.2 | 3:00<br>3:20 |
| DAP:CaCl$_2$ x 6H$_2$O:L-His:L-Arg = 1:1:3:3 + 0.5% (V/V) IBA | INITIAL<br>45 hrs/60° C. | 3.6<br>3.8 | —<br>0.2 | 3:15<br>3:45 |
| DAP:CaCl$_2$ x 6H$_2$O:L-His:L-Arg = 1:1:3:3 + 1% (V/V) EtOH | INITIAL<br>45 hrs/60° C. | 3.3<br>3.9 | —<br>0.6 | 6:00<br>6:00 |
| DAP:CaCl$_2$ x 6H$_2$O:L-His:L-Arg:Mannitol = 1:1:3:3:0.5 | INITIAL<br>45 hrs/60° C. | 3.6<br>3.8 | —<br>0.2 | 4:00<br>4:30 |
| DAP:CaCl$_2$ x 6H$_2$O:L-His:L-Arg:HPβCD = 1:1:3:3:0.1 | INITIAL<br>45 hrs/60° C. | 3.3<br>3.9 | —<br>0.6 | 3:20<br>1:10 |
| DAP:CaCl$_2$ x 6H$_2$O:L-His:L-Arg:SBEβCD = 1:1:3:3:0.1 | INITIAL<br>45 hrs/60° C. | 3.5<br>3.6 | —<br>0.1 | 3:50<br>2:00 |
| DAP:CaCl$_2$ x 6H$_2$O:L-His:L-Arg = 1:1:3:3 + 0.5% (V/V) PEG 400 + 0.2% (V/V) IBA | INITIAL<br>45 hrs/60° C. | 3.5<br>3.7 | —<br>0.2 | 2:50<br>2:55 |
| DAP:CaCl$_2$ x 6H$_2$O:L-His:L-Arg = 1:1:3:3 + 0.5% (V/V) PS 80 + 0.2% (V/V) IBA | INITIAL<br>45 hrs/60° C. | 3.5<br>3.8 | —<br>0.3 | 3:45<br>2:10 |

TABLE 5b

Stability and reconstitution times of daptomycin compositions at targeted pH 6.2

| Formulation Molar ratio | Time point/ Condition TP$_n$ | Total impurities % | Δ Total impurities % | Reconstitution time |
|---|---|---|---|---|
| DAP:CaCl2 x 2H2O:L-His:L-Arg = 1:1:3:4 + 0.25% (V/V) PPG | INITIAL<br>45 hrs/60° C. | 1.2<br>1.5 | —<br>0.3 | 0:38<br>0:45 |
| DAP:CaCl$_2$ x 2H$_2$O:L-His:L-Arg = 1:1:3:4 + 0.5% (V/V) PPG | INITIAL<br>45 hrs/60° C. | 1.6<br>2.0 | —<br>0.4 | 0:40<br>0:40 |
| DAP:CaCl$_2$ x 2H$_2$O:L-His:L-Arg = 1:1:3:3 + 2% (V/V) PPG | INITIAL<br>45 hrs/60° C. | 3.4<br>3.7 | —<br>0.3 | 0:23<br>0:20 |

The invention claimed is:

1. A lyophilized pharmaceutical composition comprising:
   a) daptomycin
   b) histidine and
   c) at least one of the following amino acids or amino acid combinations: arginine, lysine plus arginine, ornithine, phenylalanine plus tryptophan and proline plus alanine, or pharmaceutically acceptable salts thereof; wherein the molar ratio of daptomycin to each amino acid of b) and c) is from about 1:1 to about 1:5 and
   wherein the composition is a stable lyophilized composition having no more than a 2.0% increase of total impurities from an initial time point to 45 hours at 60° C. as determined by HPLC.

2. The lyophilized pharmaceutical composition according to claim 1, wherein histidine is in form of histidine hydrochloride.

3. The lyophilized pharmaceutical composition according to claim 1, wherein the composition comprises daptomycin, histidine and arginine or pharmaceutically acceptable salts thereof.

4. A method of making a pharmaceutical composition comprising reconstituting the lyophilized pharmaceutical composition according to claim 1 with a liquid diluent, wherein a concentration of daptomycin after reconstitution is from about 0.5 mg/mL to about 500 mg/mL.

5. The method of claim 4, wherein a concentration of daptomycin after reconstitution is from about 20 mg/mL to about 400 mg/mL.

6. The method of claim 4, wherein a concentration of daptomycin after reconstitution is from about 50 mg/mL to about 300 mg/mL.

7. The lyophilized pharmaceutical composition according to claim 1, wherein a molar ratio of daptomycin to each amino acid or a pharmaceutically acceptable salt thereof is from about 1:2 to about 1:5.

8. The lyophilized pharmaceutical composition according to claim 1, wherein a molar ratio of daptomycin to each amino acid or a pharmaceutically acceptable salt thereof is from about 1:3 to about 1:5.

9. The lyophilized pharmaceutical composition according to claim 1, further comprising one or more pharmaceutically acceptable excipients selected from antioxidants, surfactants, lipids, sugars, amino sugars, complexing agents, preservatives, stabilizers, bulking agents, buffers, diluents, vehicles and solubilizers.

10. A process for manufacturing compositions according to claim 1, providing a solution of daptomycin and at least one amino acid, adjusting the pH of such solution to pH from about 3 to about 9 with a suitable pH adjusting agent and lyophilizing or spray drying or fluid bed drying such composition to obtain lyophilized composition.

11. The process for manufacturing compositions according to claim 10, wherein pH is adjusted with a suitable pH adjusting agent to pH from about 4 to about 7.

12. A lyophilized pharmaceutical composition comprising:
   a) daptomycin,
   b) histidine and
   c) at least one of the following amino acids or amino acid combinations: arginine, lysine plus arginine, ornithine, phenylalanine plus tryptophan and proline plus alanine or a pharmaceutically acceptable salt thereof; wherein the molar ratio of daptomycin to at least one of amino acids of b) and c) is from about 1:1 to about 1:5 and
   wherein the composition is a stable lyophilized composition having no more than a 2.0% increase of total impurities from an initial time point to 45 hours at 60° C. as determined by HPLC.

13. The lyophilized pharmaceutical composition according to claim 12, wherein the molar ratio of daptomycin to at least one of amino acids is about 1:2 to about 1:5.

14. The lyophilized pharmaceutical composition according to claim 12, wherein the molar ratio of daptomycin to at least one of amino acids is about 1:3 to about 1:5.

* * * * *